(12) United States Patent
Herron et al.

(10) Patent No.: US 7,723,546 B1
(45) Date of Patent: May 25, 2010

(54) ARYLAMINE COMPOUNDS AND THEIR USE IN ELECTRONIC DEVICES

(75) Inventors: Norman Herron, Newark, DE (US); Nora Sabrina Radu, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1153 days.

(21) Appl. No.: 11/317,529

(22) Filed: Dec. 23, 2005

Related U.S. Application Data

(60) Provisional application No. 60/640,325, filed on Dec. 30, 2004, provisional application No. 60/694,919, filed on Jun. 28, 2005.

(51) Int. Cl.
C07C 211/00 (2006.01)
C07C 211/57 (2006.01)
C08G 73/02 (2006.01)

(52) U.S. Cl. .................. 564/433; 564/434; 564/244; 528/422

(58) Field of Classification Search .......... 528/422; 564/433, 434, 244
See application file for complete search history.

(56) References Cited

U.S. PATENT DOCUMENTS

| 6,303,238 | B1 | 10/2001 | Thompson et al. | 428/690 |
| 2001/0019782 | A1 | 9/2001 | Igarashi et al. | 428/690 |

FOREIGN PATENT DOCUMENTS

| EP | 1 191 612 A2 | 3/2002 |
| EP | 1 191 614 A2 | 3/2002 |
| GB | 2334959 | 8/1999 |
| JP | 2003 277333 | 10/2003 |
| JP | 2005 054077 | 3/2005 |
| WO | WO 00/70655 | 11/2000 |
| WO | WO 01/41512 A1 | 6/2001 |
| WO | WO 02/02714 A2 | 1/2002 |
| WO | WO 02/15645 A1 | 2/2002 |
| WO | WO 2006/088556 | 8/2006 |

OTHER PUBLICATIONS

Okada et al; Light emitting device and material therefore; Fuji Photo Film Co., Ltd., Japan; May 2002; Chem Abstract 136:377202.*
Mutaguchi, D. et al., "Development of a new class of hole-transporting and emitting vinyl polymers and their application in organic electroluminescent devices," *Orgainc Electronics*, 2003, 4, 49-59.
Campbell, I.H. et al., "Excitation Transfer Processes in a Phosphor-Doped Poly (*p*-phenylene vinylene) Light-Emitting Diode", *Physical Review B.*, vol. 65, 085210-1-085210-8, Feb. 2002.
Gustafsson, G. et al., "Flexible Light-Emitting Diodes made from Soluble Conducting Polymer", *Nature*, 1992, 357, 477-479.
O'Brien, D.F. et al., "Electrophosphoresence from a Doped Polymer Light Emitting Diode", *Synthetic Metals*, 2001, 116(1-3), 379-383.
Othmer, K., *Encyclopedia of Chemical Technology*, 1996, 18 (4th Ed), 837-860.

* cited by examiner

*Primary Examiner*—Duc Truong
(74) *Attorney, Agent, or Firm*—Woodcock Washburn LLP

(57) ABSTRACT

Provided are arylamine compounds having Formula I, II, III, or IV:

FORMULA I

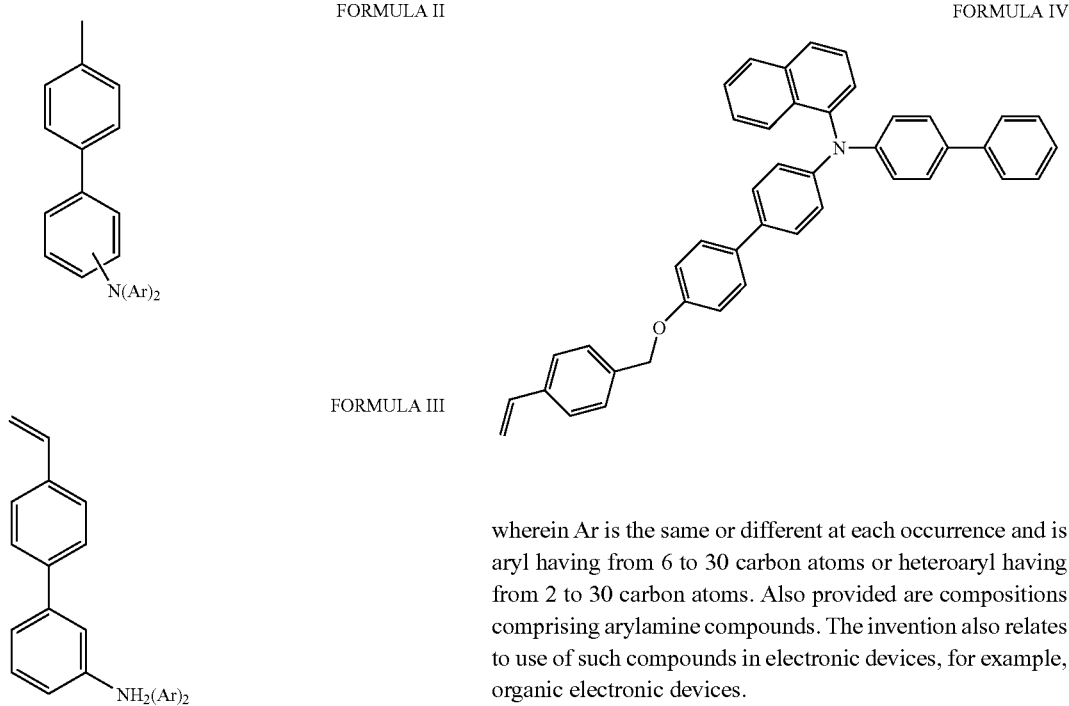
wherein Ar is the same or different at each occurrence and is aryl having from 6 to 30 carbon atoms or heteroaryl having from 2 to 30 carbon atoms. Also provided are compositions comprising arylamine compounds. The invention also relates to use of such compounds in electronic devices, for example, organic electronic devices.
4 Claims, 3 Drawing Sheets

ARYLAMINE COMPOUNDS AND THEIR USE IN ELECTRONIC DEVICES

CROSS-REFERENCE TO RELATED APPLICATIONS

The present application claims benefit to U.S. Provisional Application Ser. Nos. 60/640,325 filed Dec. 30, 2004 and 60/694,919, filed Jun. 28, 2005, each of which are incorporated herein by reference in their entireties.

FIELD OF THE DISCLOSURE

This disclosure relates generally to arylamine compounds, for example, their use in organic electronic devices, and materials and methods for fabrication of the same.

BACKGROUND OF THE DISCLOSURE

Organic electronic devices convert electrical energy into radiation, detect signals through electronic processes, convert radiation into electrical energy, or include one or more organic semiconductor layers. Most organic electronic devices include a conductive layer (such as a light-emitting or photoactive layer) positioned between two electrodes. In some devices, a charge transport layer can be utilized between the conductive layer and an electrode. For example, a hole transport layer can be positioned between the conductive layer and the anode and a electron transport layer can be positioned between the conductive layer and the cathode.

Thus, what is needed are new materials for use in organic electronic devices.

SUMMARY

In one embodiment, provided are arylamine compounds having Formula I, II, III, or IV:

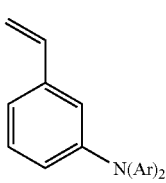

FORMULA I

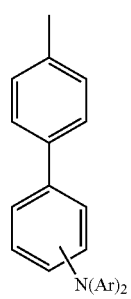

FORMULA II

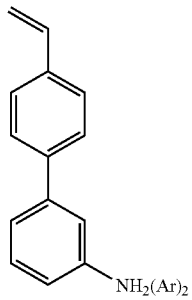

FORMULA III

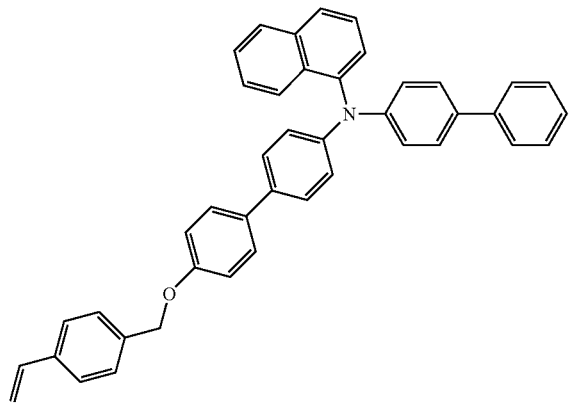

FORMULA IV wherein Ar is the same or different at each occurrence and is aryl having from 6 to 30 carbon atoms or heteroaryl having from 2 to 30 carbon atoms.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
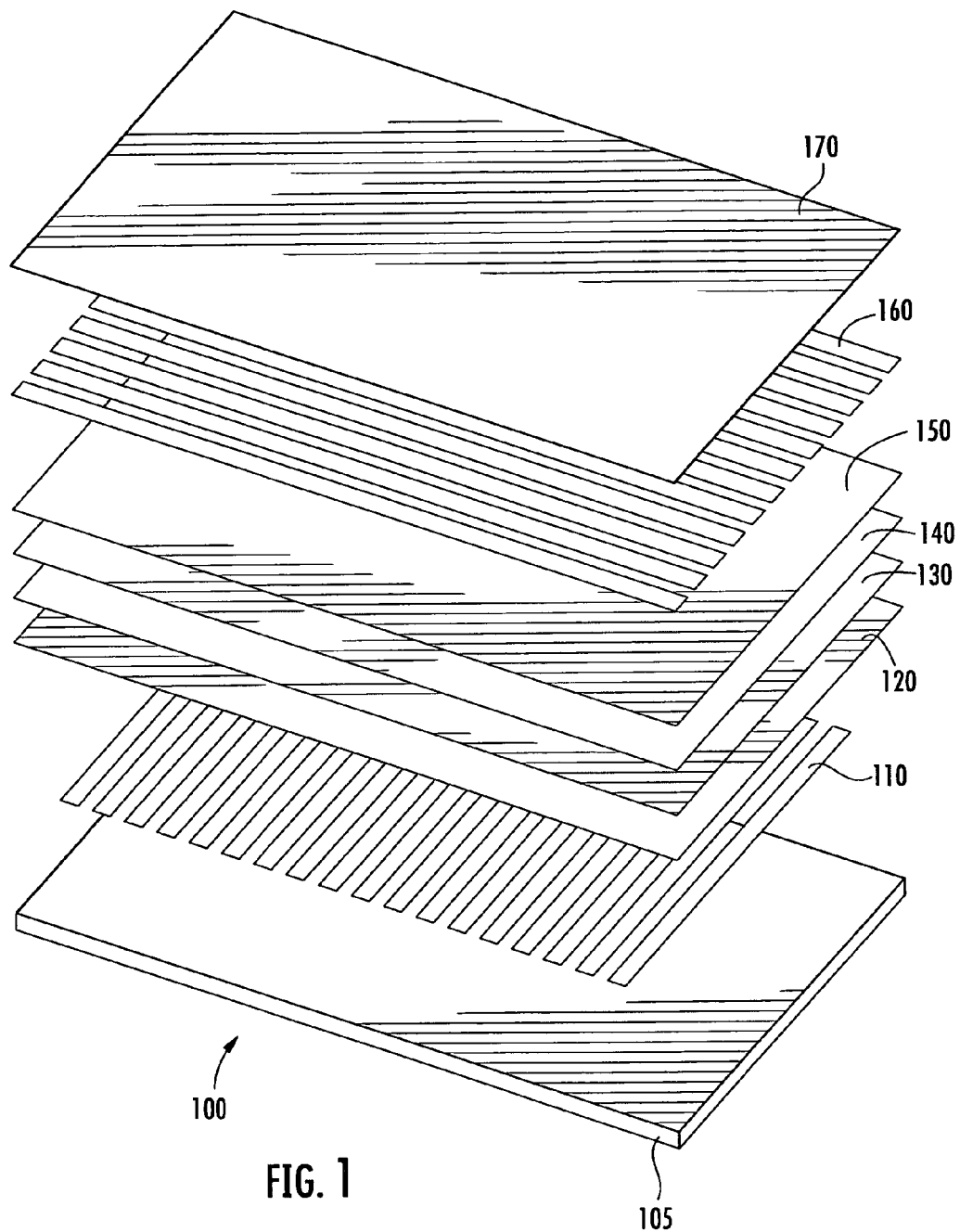
FIG. 1 includes an illustrative example of an organic electronic device that contains at least one layer having at least one arylamine compound.

The figures are provided by way of example and are not intended to limit the invention. Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

In one embodiment, provided are arylamine compounds having Formula I:

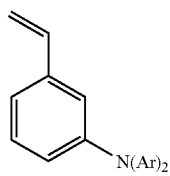

Formula I wherein Ar is the same or different at each occurrence and is aryl having from 6 to 30 carbon atoms or heteroaryl having from 2 to 30 carbon atoms.

In one embodiment, provided are arylamine compounds having Formula II:

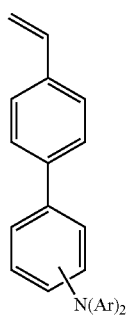

Formula II wherein Ar is the same or different at each occurrence and is aryl having from 6 to 30 carbon atoms or heteroaryl having from 2 to 30 carbon atoms.

In one embodiment, provided are arylamine compounds having Formula III:

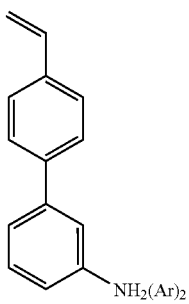

Formula III wherein Ar is the same or different at each occurrence and is aryl having from 6 to 30 carbon atoms or heteroaryl having from 2 to 30 carbon atoms.

In one embodiment, in compounds of Formula I, II, or III, Ar is phenyl or naphthyl.

In one embodiment, provided are arylamine compounds having Formula IV:

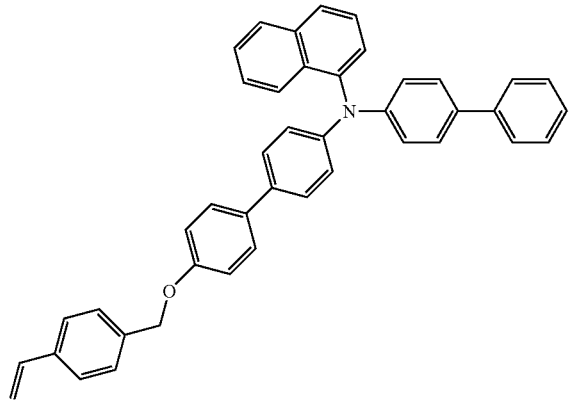

Formula IV

In one embodiment, provided are arylamine compounds having Formulas VI, VII, or VIII:

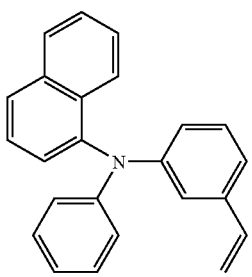

Formula VI

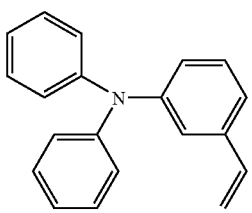

Formula VII

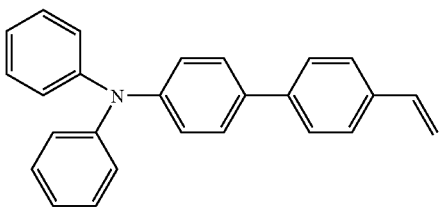

Formula VIII

In one embodiment, one or more of the arylamine compounds can be admixed with a polymer.

In one embodiment, provided is a polymer having Formula V:

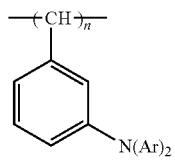

Formula V wherein Ar is the same or different at each occurrence and is aryl having from 6 to 30 carbon atoms or heteroaryl having from 2 to 30 carbon atoms and n is an integer from 3 to 1000.

In one embodiment, provided is a polymer comprising at least one monomeric unit derived from at least one compound having Formula I, II, III, IV, VI, VII, or VIII.

In one embodiment, the polymer is a random, block, graft, or alternating copolymer.

In one embodiment, the polymer is a homopolymer. In one embodiment, the polymer is a copolymer having two or more different monomeric units derived from compounds having Formula I, II, III, IV, VI, VII, or VIII. In one embodiment, the polymer is a copolymer having at least one monomeric unit derived from a compound having Formula I, II, III, IV, VI, VII, or VIII, and at least one monomeric unit derived from a second monomer. The second monomer can be a conjugated compound having a vinyl substituent. Examples of conjugated compounds include, but are not limited to, arylenes, fluorenes, bifluorenes and dibenzosiloles, all of which may be substituted or unsubstituted. The polymers can be prepared using well known vinyl polymerization methods.

In one embodiment, the arylamine compounds have charge transport properties. For example, the compound may have hole transport properties. In one embodiment, a hole transport layer can comprise an arylamine compound.

In one embodiment, the arylamine polymers have a glass transition temperature ("$T_g$") that is higher than other commonly used arylamine compounds. In one embodiment, the materials with higher $T_g$ form better films when deposited by either vapor or solution processing methods. In one embodiment, the $T_g$ is greater than 125° C. In one embodiment, the $T_g$ is greater than 130° C.

In one embodiment of the invention, at least one of the arylamine compounds are included in at least one layer of an electronic device. In one embodiment, at least one of the arylamine compounds is included in a charge transport layer. In one embodiment, at least one of the arylamine compounds is included in a photoactive layer.

In one embodiment, the invention provides electronic devices comprising at least one layer comprising a compound described herein. In one embodiment, the device is an organic light-emitting diode, a diode laser, a photodetector, a photoconductive cell, a photoresistor, a photoswitch, a phototransistor, a phototube, an IR detector, a photovoltaic cell, a solar cell, a light sensor, a thin film organic transistor, a photoconductor, or an electrophotographic device.

In one embodiment, the invention provides a composition comprising at least one arylamine compound and at least one of a solvent, a process aid, or a polymer.

In one embodiment, articles useful in the manufacture of an organic electronic device comprising the compounds described herein are provided.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Illustrative Electronic Devices, and finally Examples.

1. DEFINITIONS AND CLARIFICATION OF TERMS

Before addressing details of embodiments described below, some terms are defined or clarified.

As used herein, the term "alkyl" includes both branched and straight-chain saturated aliphatic hydrocarbon groups having the specified number of carbon atoms. Unless otherwise indicated, the term is also intended to include cyclic groups. Examples of alkyl groups include methyl, ethyl, propyl, isopropyl, isobutyl, secbutyl, tertbutyl, pentyl, isopentyl cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. On example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms.

The term "aryl" means an aromatic carbocyclic moiety of up to 30 carbon atoms, which may be a single ring (monocyclic) or multiple rings (bicyclic, up to three rings) fused together or linked covalently. Any suitable ring position of the aryl moiety may be covalently linked to the defined chemical structure. The aryl group may be unsubstituted or substituted. Examples of aryl moieties include, but are not limited to, phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments, aryl groups have 6 to 20 carbon atoms.

The term "heteroaryl," as used herein, refers to a $C_2$ to $C_{30}$ monocyclic or bicyclic carbon containing aromatic ring having 1 to 3 of its ring members independently selected from nitrogen, sulfur or oxygen. In some embodiments, monocyclic rings have 5 to 6 members. In certain embodiments, bicyclic rings have 8 to 10 membered ring structures. The heteroaryl group may be unsubstituted or substituted. Examples of heteroaryls include, but are not limited to, thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, and quinazolinyl.

An optionally substituted group, such as aryl, or heteroaryl, can be substituted with one or more substituents which may be the same or different. Suitable substituents include alkyl, aryl, nitro, cyano, —N($R^1$)($R^2$), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, thioalkyl, —S(O)$_2$—N($R^1$)($R^2$), —C(=O)—N($R^1$)($R^2$), ($R^1$)($R^2$)N-alkyl, ($R^1$)($R^2$)N-alkoxyalkyl, ($R^1$)($R^2$)N-alkylaryloxyalkyl, —S(O)$_s$aryl (where s=0-2) or —S(O)$_s$-heteroaryl (where s=0-2). Each $R^1$ and $R^2$ is independently an optionally substituted alkyl, or aryl group. $R^1$ and $R^2$, together with the nitrogen atom to which they are bound, can optionally form a ring system.

The prefix "hetero" indicates that one or more carbon atoms has been replaced with a different atom.

The term "group" is intended to mean a part of a compound, such as a substituent in an organic compound.

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photoswitches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode). The term device also includes coating materials for memory storage devices, antistatic films, biosensors, electrochromic devices, solid electrolyte capacitors, energy storage devices such as a rechargeable battery, and electromagnetic shielding applications.

The term "substrate" is intended to mean a workpiece that can be either rigid or flexible and may include one or more layers of one or more materials, which can include, but are not limited to, glass, polymer, metal, or ceramic materials, or combinations thereof.

The term "active" when referring to a layer or material is intended to mean a layer or material that exhibits electronic or electro-radiative properties. An active layer material may emit radiation or exhibit a change in concentration of electron-hole pairs when receiving radiation. Thus, the term "active material" refers to a material which electronically facilitates the operation of the device. Examples of active materials include, but are not limited to, materials which conduct, inject, transport, or block a charge, where the charge can be either an electron or a hole. Examples of inactive materials include, but are not limited to, planarization materials, insulating materials, and environmental barrier materials.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector). An example of a photoactive layer is an emitter layer.

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

The term "monomer" refers to a compound capable of being polymerized. The term "monomeric unit" refers to units which are repeated in a polymer.

The term "polymeric" is intended to encompass oligomeric species and include materials having 2 or more monomeric units. A polymer having repeating units derived from a monomer

will have repeating units

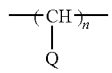

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms which are joined by a bond).

As used herein, the term "charge transport," when referring to a layer or material is intended to mean such layer or material facilitates migration of such charge through the thickness of such layer, material, member, or structure with relative efficiency and small loss of charge, and is meant to be broad enough to include materials that may act as a hole transport or an electron transport material. The term "hole transport" when referring to a layer or material means such a layer or material, member or structure that promotes or facilitates migration of positive charge, or "holes", through such a layer or material into another layer, material, member or structure. The term "electron transport" when referring to a layer or material means such a layer or material, member or structure that promotes or facilitates migration of electrons through such a layer or material into another layer, material, member or structure.

The term "charge blocking," when referring to a layer, material, member, or structure, is intended to mean such layer, material, member or structure reduces the likelihood that a charge migrates into another layer, material, member or structure. The term "electron blocking" when referring to a layer, material, member or structure is intended to mean such layer, material, member or structure that reduces that likelihood that electrons migrate into another layer, material, member or structure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The use of "a" or "an" are employed to describe elements and components of the invention. This is done merely for convenience and to give a general sense of the invention. This description should be read to include one or at least one and the singular also includes the plural unless it is obvious that it is meant otherwise.

Group numbers corresponding to columns within the Periodic Table of the elements use the "New Notation" convention as seen in the CRC Handbook of Chemistry and Physics, 81st Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. ILLUSTRATIVE ELECTRONIC DEVICES

Referring to FIG. 1, an exemplary organic electronic device 100 is shown. The device 100 includes a substrate 105. The substrate 105 may be rigid or flexible, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. Anode layers may be deposited as lines. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in Flexible Light-Emitting Diodes Made From Soluble Conducting Polymer, Nature 1992, 357, 477-479. At least one of the anode and cathode should be at least partially transparent to allow the generated light to be observed.

An optional hole transport layer 120, comprising hole transport materials, may be deposited over the anode layer 110, the latter being sometimes referred to as the "hole-injecting contact layer." The arylamine compounds and polymers described herein may be used in the hole transport layer 120. Examples of other hole transport materials suitable for use as the layer 120 have been summarized, for example, in Kirk Othmer, Encyclopedia of Chemical Technology, Vol. 18, 837-860 (4th ed. 1996). Both hole transporting "small" molecules as well as oligomers and polymers may be used. Hole transporting molecules include, but are not limited to: N,N' diphenyl-N,N'-bis(3-methylphenyl)-[1,1'-biphenyl]-4,4'-diamine (TPD), 1,1 bis[(di-4-tolylamino) phenyl]cyclohexane (TAPC), N,N' bis(4-methylphenyl)-N,N'-bis(4-ethylphenyl)-[1,1'-(3,3'-dimethyl)biphenyl]-4,4'-diamine (ETPD), tetrakis (3-methylphenyl)-N,N,N',N'-2,5-phenylenediamine (PDA), a-phenyl 4-N,N-diphenylaminostyrene (TPS), p (diethylamino)benzaldehyde diphenylhydrazone (DEH), triphenylamine (TPA), bis[4 (N,N-diethylamino)-2-methylphenyl](4-methylphenyl)methane (MPMP), 1 phenyl-3-[p-(diethylamino) styryl]-5-[p-(diethylamino)phenyl]pyrazoline (PPR or DEASP), 1,2 trans-bis(9H-carbazol-9-yl)cyclobutane (DCZB), N,N,N',N' tetrakis(4-methylphenyl)-(1,1'-biphenyl)-4,4'-diamine (TTB), and porphyrinic compounds, such as copper phthalocyanine. Useful hole transporting polymers include, but are not limited to, polyvinylcarbazole, (phenylmethyl)polysilane, and polyaniline. Conducting polymers are useful as a class. It is also possible to obtain hole transporting polymers by doping hole transporting moieties, such as those mentioned above, into polymers such as polystyrenes and polycarbonates.

An organic layer 130 may be deposited over the hole transport layer 120 when present, or over the first electrical contact layer 110. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

Any organic electroluminescent ("EL") material can be used as a photoactive material (e.g., in layer 130). Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum ($Alq_3$); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the devices of the invention, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. 2001, 116 (1-3), 379-383, and Campbell et al., in Phys. Rev. B, Vol. 65 085210. The arylamine compounds and polymers described herein can be used as a host material for electroluminescent complexes.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used. Lithium-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be a buffer layer (not shown) between the anode 110 and hole transport layer 120 to facilitate positive charge transport and/or band-gap matching of the layers, or to function as a protective layer. Other layers that are known in the art or otherwise may be used. In addition, any of the above-described layers may comprise two or more sub-layers or may form a laminar structure. Alternatively, some or all of anode layer 110 the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

Devices can be prepared employing a variety of techniques. These include, by way of non-limiting exemplification, vapor deposition techniques and liquid deposition.

Devices may also be sub-assembled into separate articles of manufacture that can then be combined to form the device.

3. EXAMPLES

The concepts described herein will be further described in the following examples, which do not limit the scope of the invention described in the claims.

All percentages are by weight, unless otherwise indicated.

Example 1

This example illustrates the preparation of the arylamine compound below:

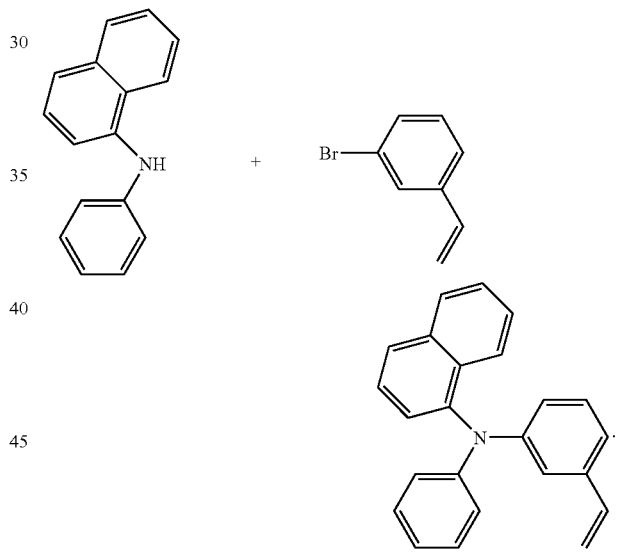

Figure 2:
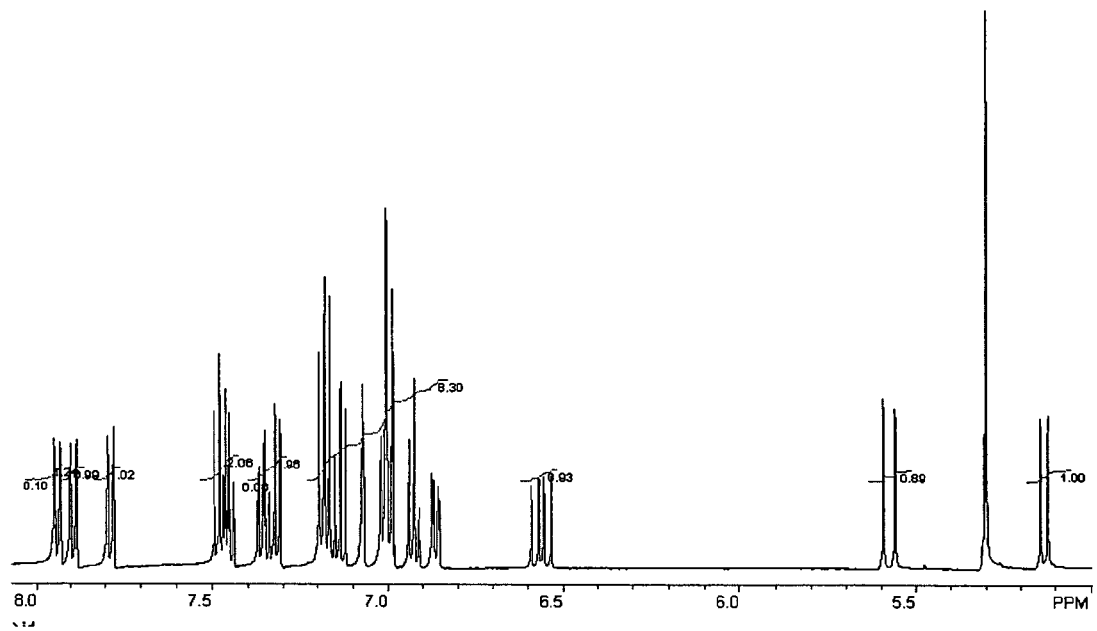
FIG. 2 depicts IR spectrum of product discussed in Example 1.

A mixture of phenyl(1-naphthyl)amine (10 g, 45.0 mmol), 3-bromostyrene (9.2 g, 50.0 mmol), NaO'Bu (5.1 g, 55.0 mmol), $Pd_2(dba)_3$ (0.300 g, 0.33 mmol) and $P('Bu)_3$ (0.150 g, 0.74 mmol) was stirred in toluene (80 mL) under nitrogen for 20 hours. The resulting solution was diluted with diethylether and filtered through celite and silica. Upon evaporation of the solvent a dark brown viscous material was obtained which was purified by chromatography on silica (hexanes) and the desired product was obtained as a white solid (9.8 g, 67%). See FIG. 2.

Example 2

This example illustrates the preparation of the arylamine compound below:

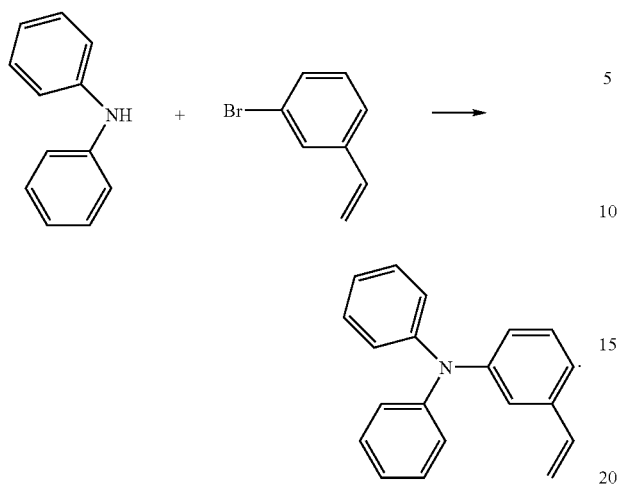

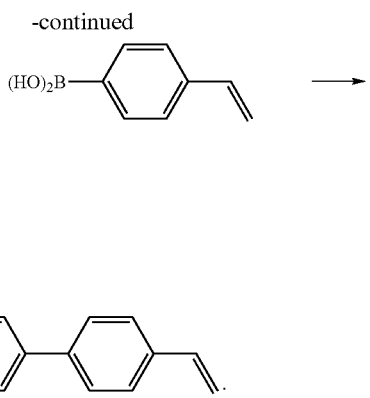

Figure 3:
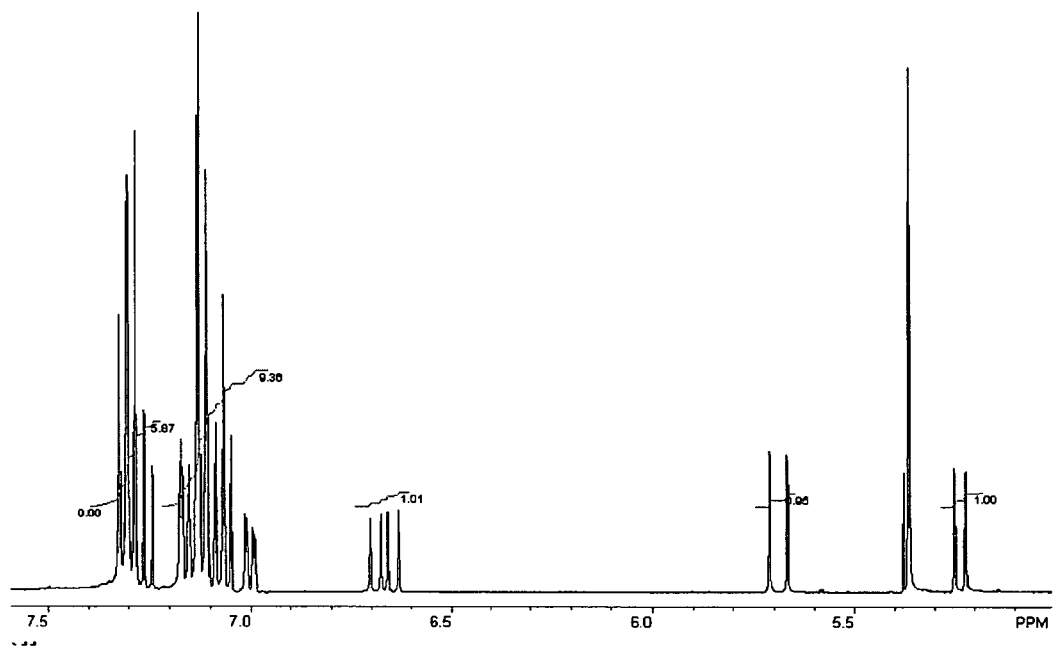
FIG. 3 depicts IR spectrum of product discussed in Example 2.

A mixture of diphenylamine (4.6 g, 27.0 mmol), 3-bromostyrene (5.0 g, 27.0 mmol), NaO$^t$Bu (3.0 g, 38.0 mmol), Pd$_2$(dba)$_3$ (0.300 g, 0.33 mmol) and P($^t$Bu)$_3$ (0.150 g, 0.74 mmol) was stirred in toluene (80 mL) under nitrogen for 20 hours. The resulting solution was diluted with diethylether and filtered through celite and silica. Upon evaporation of the solvent a dark brown viscous material was obtained which was purified by chromatography on silica (hexanes) and the desired product was obtained as a white solid (4.25 g, 65% yield). See FIG. 3.

Example 3

This example illustrates the preparation of the arylamine compound below:

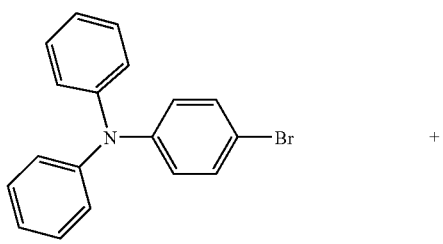

| | | | | |
|---|---|---|---|---|
| NPh$_2$(PhBr) | 324.210 | 1.54E−02 | 5.000 | 1.000 |
| styreneB(OH)$_2$ | 147.970 | 1.70E−02 | 2.510 | 1.100 |
| Pd(PPh$_3$)$_4$ | 1155.570 | 7.71E−04 | 0.891 | 0.050 |
| K$_2$CO$_3$ | 138.210 | 5.94E−02 | 8.206 | 3.500 |
| product | 347.450 | 1.54E−02 | 5.351 | |

Figure 4:
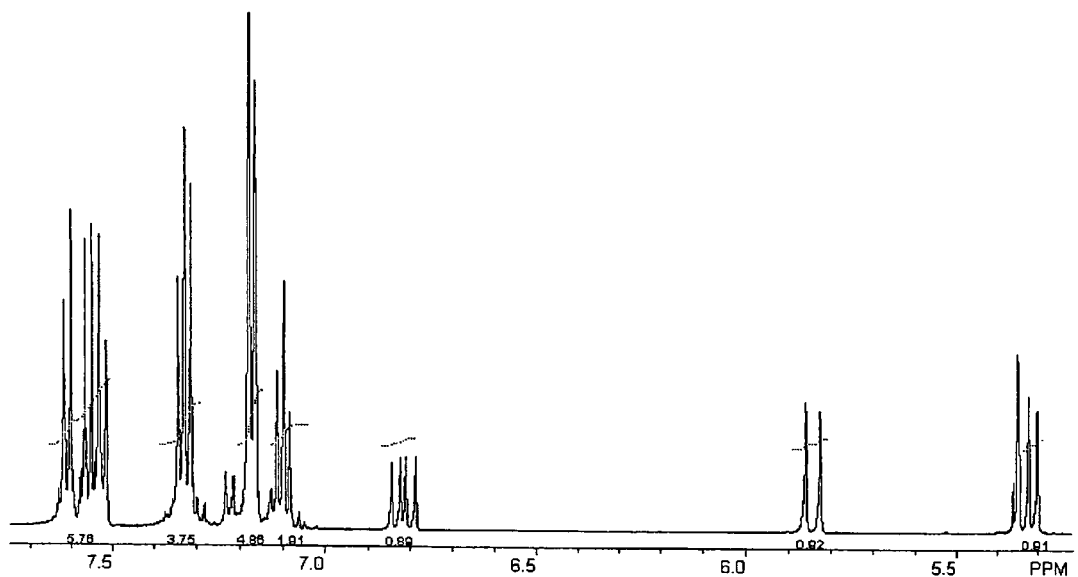
FIG. 4 depicts IR spectrum of product discussed in Example 3.

A degassed solution of K$_2$CO$_3$ (8.20 g, 15.4 mmol) in H$_2$O (100 mL) was added to a mixture of (4-bromophenyl)diphenyl amine (5.00 g, 1.54 mmol), 4-(vinyl)phenylboronic acid (3.53 g, 18.2 mmol) and Pd(PPh$_3$)$_4$ (0.89 g, 0.77 mmol) in monoglyme (100 mL) and then heated to 8° C. overnight. Upon cooling, the mixture was diluted with diethylether and 1 M HCl(~10 mL) was added. After neutralization with a saturated solution of NaHCO$_3$, the organic layer was separated and dried over MgSO$_4$. Upon evaporation of the solvent a yellow solid was obtained which was purified by chromatography on silica (hexane) to obtain the desired product as a white powder (2.2 g, 41%). See FIG. 4.

Example 4

This example illustrates the preparation of the arylamine compound below:

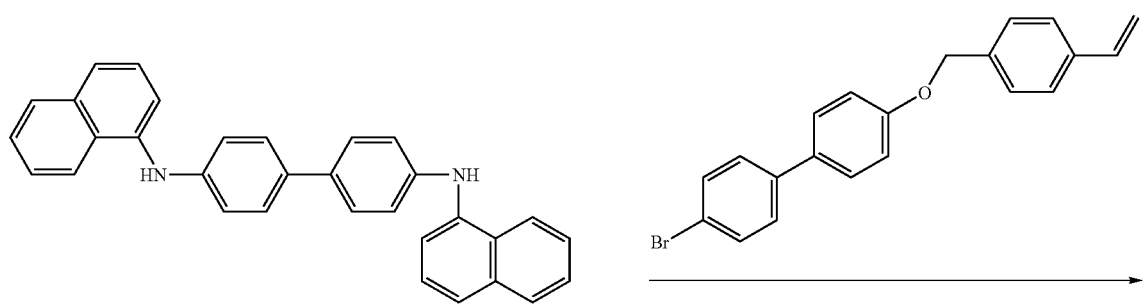

-continued

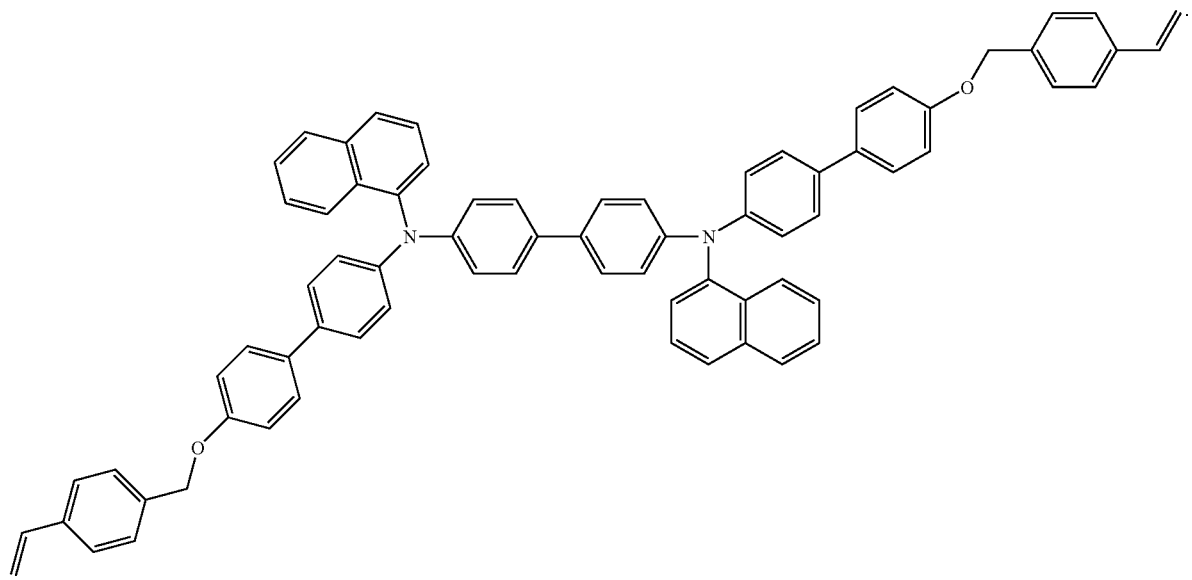

Figure 5:
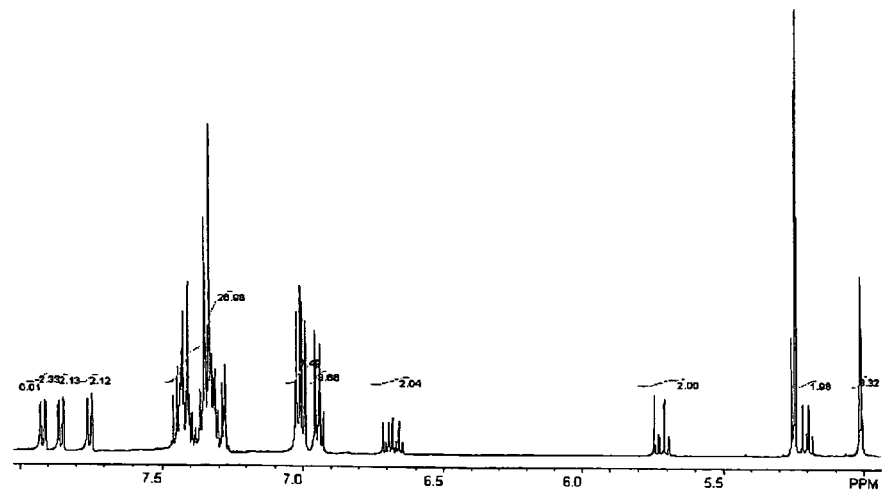
FIG. 5 depicts IR spectrum of product discussed in Example 4.

A mixture of N,N'-di(1-naphthyl)benzidine (2.16 g, 4.9 mmol), 4-bromo-1,1'-biphenyl-4'-(p,m-vinyl)benzyl (3.8 g, 10 mmol), NaO'Bu (1.15 g, 12 mmol), Pd$_2$(dba)$_3$ (0.300 g, 0.33 mmol) and P('Bu)$_3$ (0.150 g, 0.74 mmol) was stirred in toluene (30 mL) under nitrogen for 20 hours. The resulting solution was diluted with diethylether and filtered through celite and silica. Upon evaporation of the solvent a dark brown viscous material was obtained. Addition of hexane produced a yellow powder, which was isolated by filtration. Further purification from CH$_2$Cl$_2$/hexane gave the desired product (1.63 g, 33%). See FIG. 5.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Many aspects and embodiments have been described above and are merely exemplary and not limiting. After reading this specification, skilled artisans appreciate that other aspects and embodiments are possible without departing from the scope of the invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed:
1. A compound of Formula I, II, or IV:

Formula I

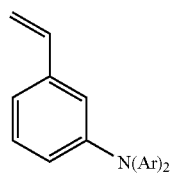

Formula II

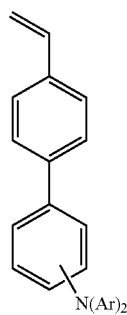

FORMULA IV

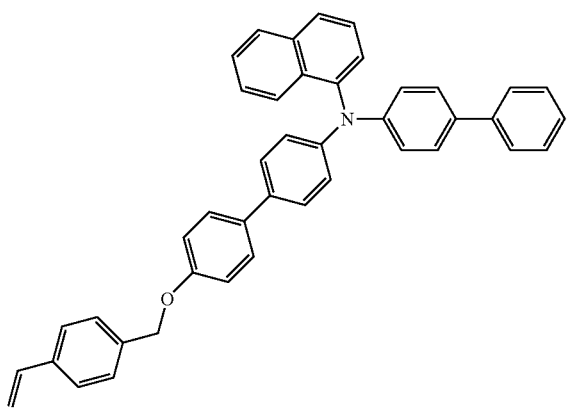

wherein Ar is the same or different at each occurrence and is phenyl, naphthyl or heteroaryl having from 2 to 30 carbon atoms, said phenyl, naphthyl, or heteroaryl being optionally substituted with one or more groups selected from alkyl, aryl, nitro, cyano, —N(R$^1$)(R$^2$), hydroxy, carboxy, alkenyl, alkynyl, cycloalkyl, alkoxy, aryloxy, heteroaryloxy, alkoxycarbonyl, perfluoroalkyl, perfluoroalkoxy, arylalkyl, thioalkyl, —S(O)$_2$—N(R$^1$)(R$^2$), —C(=O)—N(R$^1$)(R$^2$), (R$^1$)(R$^2$)N-alkyl, (R$^1$)(R$^2$)N-alkoxyalkyl, (R$^1$)(R$^2$)N-alkylaryloxyalkyl, —S(O)$_s$-aryl or —S(O)$_s$-heteroaryl, where s is 0, 1 or 2 and each R$^1$ and R$^2$ is independently an optionally substituted alkyl, or aryl group; or R$^1$ and R$^2$, together with the nitrogen atom to which they are bound, optionally form a ring system.

2. A compound of claim 1 wherein Ar is phenyl or naphthyl.

3. A composition including the compound of claim 1.

4. The compound of claim 1 comprising the formula:

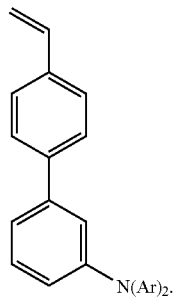

Formula III wherein Ar is defined in claim 1.

* * * * *